(12) United States Patent
Khashman

(10) Patent No.: US 12,260,072 B1
(45) Date of Patent: Mar. 25, 2025

(54) SYSTEMS AND METHODS FOR CONCURRENTLY HANDLING MULTIPLE ARTIFACT TYPES IN A UNIFIED GRAPHICAL USER INTERFACE

(71) Applicant: Technology Partners LLC, Charlotte, NC (US)

(72) Inventor: Sam Faris Khashman, Charlotte, NC (US)

(73) Assignee: Technology Partners LLC, Charlotte, NC (US)

( * ) Notice: Subject to any disclaimer, the term of this patent is extended or adjusted under 35 U.S.C. 154(b) by 0 days.

(21) Appl. No.: 18/940,970

(22) Filed: Nov. 8, 2024

Related U.S. Application Data

(60) Provisional application No. 63/547,983, filed on Nov. 9, 2023.

(51) Int. Cl.
| | |
|---|---|
| *G06F 3/0484* | (2022.01) |
| *G06F 3/0482* | (2013.01) |
| *G06F 40/177* | (2020.01) |
| *G06Q 10/10* | (2023.01) |
| *G16H 10/60* | (2018.01) |

(52) U.S. Cl.
CPC .......... *G06F 3/0484* (2013.01); *G06F 3/0482* (2013.01); *G06F 40/177* (2020.01); *G06Q 10/10* (2013.01); *G16H 10/60* (2018.01); *G06F 2203/04803* (2013.01)

(58) Field of Classification Search
CPC .... G06F 3/0484; G06F 3/0482; G06F 40/177; G06F 2203/04803; G06Q 10/10; G16H 10/60
See application file for complete search history.

(56) References Cited

U.S. PATENT DOCUMENTS

| | | | | |
|---|---|---|---|---|
| 2007/0100659 | A1* | 5/2007 | Preiss | G16H 10/20 705/2 |
| 2022/0197455 | A1* | 6/2022 | Xu | G06F 40/18 |
| 2023/0252904 | A1* | 8/2023 | Ikebe | G09B 19/00 |
| 2023/0274809 | A1* | 8/2023 | Dimitrova | G06F 8/34 705/3 |

* cited by examiner

*Primary Examiner* — Nicholas Ulrich
(74) *Attorney, Agent, or Firm* — Padowithz Alce; Alce PLLC

(57) ABSTRACT

A method for concurrently handling multiple artifact types includes displaying a multi-artifact handling user interface for concurrently handling a corpus of exception artifacts and a corpus of validated artifacts, wherein the multi-artifact handling user interface includes: a first dynamic artifact user interface component that displays the corpus of exception artifacts in an editable state during a first period, a second dynamic artifact user interface component that displays the corpus of validated artifacts in an un-editable state during the first period, and a transition control toggle button that is selectable to transition: the first dynamic artifact user interface component from displaying the corpus of exception artifacts to displaying the corpus of validated artifacts during a second period, and the second dynamic artifact user interface component from displaying the corpus of validated artifacts to displaying the corpus of exception artifacts during the second period.

20 Claims, 15 Drawing Sheets

200

Identifying a Set of Unposted Artifacts S210

Modifying at least one Artifact (or Artifact Exception) in the Set of Unposted Artifacts S220

Re-Validating Modified Exceptions or Validated Artifacts S230

Posting Validated Artifacts S240

*Imagine* one

Home

Charge

Billing

Patient

Payment

Follow Up

Contract

Performance

System

Home | Tickler Main × | Account Inquiry ×

Batch Number: ERS_SDI_026_03432_269_12_202

[New] [Refresh]

| ID | Patient ID | Exception Message | Reason Code | Patient Name |
|---|---|---|---|---|
| 7219898 | 0 | PLB Provider Level Adjustment information included in remittance file,1 | | GOOD, GREG G |
| 7219902 | 0 | PLB Provider Level Adjustment information included in remittance file,1 | | ERIKSSON, ELOY E |
| 7219906 | 0 | PLB Provider Level Adjustment information included in remittance file,1 | | EINARRSON, EMORY E |
| 7219896 | 0 | PLB Provider Level Adjustment information included in remittance file,1 | | VAZQUEZ, VIRGIL V |
| 7219900 | 0 | PLB Provider Level Adjustment information included in remittance file,1 | | |
| 7219904 | 0 | PLB Provider Level Adjustment information included in remittance file,1 | | |

[Delete]

Charge Information

Payment ID | | Procedure

| Patient ID | Patient Name | Visit Number | Location | POS Code |
|---|---|---|---|---|

Insurance Information

○ Primary    ○ Secondary

Payment Information

Payment Type | Charge: 1 | Payment Source | Insurance Policy

Payment$ $0.00 | Adj$ $0.00 | Allowed$ $0.00 | Coins$ $0.00 | Deduct$ $0.00 | Copay$ $0.00 | Withhold$ $0.00

Denial | Adjustment Type

FIG. 4

ERS Central ✕

Stage (All) | File Name (All)

O

| Insurance Carrier Name | Date of Service | Procedure Code | Charge Amount |
|---|---|---|---|
| United Healthcare | 01/01/1900 | | $0.00 |
| United Healthcare | 01/01/1900 | | $0.00 |
| United Healthcare | 01/01/1900 | | $0.00 |
| United Healthcare | 01/01/1900 | | $0.00 |

Unposted ERS Batch Number

Batch Number | Insurance Carrier | Check Number | Patient ID | Search

359 Unposted ERS Batch Number

| Batch Number | Min. Import Date | Max. Import Date | Payment Count |
|---|---|---|---|
| ERS_SDI_IMG_PA994_0_NOPAY_2704107_12_30_20 | 12/10/2022 | 12/10/2022 | 1 |
| ERS_SDI_IMG_TWCCN_67.01_11558012_20221219_12_30_20 | 01/03/2023 | 01/03/2023 | 1 |
| ERS_SDI_IMG_U6885_252.41_27227431_20220915_09_26_2 | 09/26/2022 | 09/26/2022 | 1 |
| ERS_SDI_IMG_WYBLS_O_NOPAY_2651014_20221020_11_21_2 | 11/21/2022 | 11/21/2022 | 10 |
| ERS_SDI_IMG_WYBLS_32.42_10226170_20221104_11_25_20 | 11/25/2022 | 11/25/2022 | 1 |

Select | Close

○ Teritary    ○ Other    Insurance

Rule Info    Other Payments    Review (0)

Vehicle$ $0.00 | App$ $0.00 | Balance$ $0.00 | Charge$ $0.00 | Rem$ $0.00

ICN | Withhold Adjustment Type

| Patient ID | Insurance Carrier Name | Service Date |
|---|---|---|

Note

☐ Force Hold in Verification    Save

FIG. 4(Cont...)

Unmapped Payers

| Payment Amount | Claim Number | Adjustment Amount | Approved Amount | Insured ID | File Do |
|---|---|---|---|---|---|
| ($3.64) | | ($0.00) | | | |
| ($64.98) | | ($0.00) | | | |
| ($3.64) | | ($0.00) | | | |
| ($1.14) | | ($0.00) | | | |
| ($70.00) | | ($0.00) | | | |
| ($70.00) | | ($0.00) | | | |

| Post Date | ICD10.Diagnosis | Primary Insurance | Secondary Insurance |
|---|---|---|---|

Lock

0 Payments

| Procedure Code | Charge Amount | Payment Amount | Adjustment Amount |
|---|---|---|---|

FIG. 4(Cont...)

*Imagine* one

Home

Charge

Billing

Patient

Payment

Follow Up

Contract

Performance

System

Home | Tickler Main ✕ | Account Inquiry ✕

Batch Number: ERS_SDI_IMG_WYBLS_0_NOPAY    [New]  [Refresh]

| ID | Patient ID | Exception Message | Reason Code |
|---|---|---|---|
| 7296964 | 763700 | ERS Payment Mapping Needed | CO129 |
| 7296968 | 763700 | ERS Payment Mapping Needed | CO45 |
| 7296966 | 763700 | ERS Payment Mapping Needed | CO45 |
| 7296972 | 0 | FLB Provider Level Adjustment information included in remittance file,1 | |
| 7242163 | 763700 | ERS Payment Mapping Needed | CO129 |
| 7206067 | 763700 | ERS Payment Mapping Needed | CO45 |

[Delete]

Charge Information

Patient ID: 763700    HERRING, HARRIETT H    Procedure: 76376

| Patient ID | Patient Name | Visit Number | Location | POS Code |
|---|---|---|---|---|
| 763700 | HERRING, HARRIETT H | 1095972202003 11083000ICR | 103 - Imagine Demo Location 103 | 11 |

Insurance Information

○ Primary - 138885-Insurance Plan 138885 (1 - MCADC)    ○ Secondary - 65912 - Insurance Plan 65912(5 - COMM)

Payment Information

Payment Type: Payment    Charge: 1    Payment Source:    Insurance Policy:

| Payment$ | Adj$ | Allowed$ | Coins$ | Deduct$ | Copay$ | Withhold |
|---|---|---|---|---|---|---|
| $0.00 | $0.00 | $0.00 | $0.00 | $0.00 | $0.00 | $0.00 |

Denial:    Adjustment Type:

FIG. 5

| ERS Central | × | | |
|---|---|---|---|

Stage: (All)   File Name:

8 Exceptions

| Patient Name | Insurance Carrier Name | Date of Service | Procedure Code |
|---|---|---|---|
| HERRING HARRIETT H | BCBS - Other | 03/11/2020 | 74177 |
| HERRING HARRIETT H | MEDICARE | 03/11/2020 | 76376 |
| HERRING HARRIETT H | MEDICARE | 03/11/2020 | 71260 |
| CHAVEZ, CLARK C | BCBS - Other | 01/01/1900 | |
| HERRING HARRIETT H | BCBS - Other | 03/11/2020 | 71260 |
| HERRING HARRIETT H | MEDICARE | 03/11/2020 | 74177 |

Date of Service: 3/11/2020   Level:   ICN:   ○ Unlock

1 Charge

| Doctor | Date of Service | Procedure | Modifier |
|---|---|---|---|
| 43 - BIRD, BRETT B | 3/11/2020 12:00AM | 76376 - 3D rendering with interpretation and reporting pf computed to | 26 |

○ Teritary - None     ○ Other   Insurance:

Rule Info   Other Payments   Review(2)

| Vehicle$ | App$ | Balance$ | Charge$ | Rem$ |
|---|---|---|---|---|
| $0.00 | $0.00 | $0.00 | $0.00 | $0.00 |

ICN:   Withhold Adjustment Type:

Note:

| Patient ID | Insurance Carrier Name | Service Date |
|---|---|---|
| 763700 | BCBS - Other | 03/11/2020 |
| 763700 | BCBS - Other | 03/11/2020 |

○ Force Hold in Verification   [Save]

[Unmapped Payers] [Capture Options]

FIG. 5(Cont...)

| Charge Amount | Payment Amount | Claim Number | Adjustment Amount |
|---|---|---|---|
| $1,048.00 | $10.00 | 21493033250 | $0.00 |
| $82.00 | $0.00 | 21435672292 | $0.00 |
| $592.00 | $100.00 | 21435672292 | $0.00 |
| $0.00 | ($18.40) | | $0.00 |
| $592.00 | $0.00 | 21493033250 | $592.00 |
| $1048.00 | $0.00 | 21425672202 | $0.00 |

Distribute  Action ▽  Copy

| Units | Order Number | Charge Amount |
|---|---|---|
| 1.00 | 8B9B4D434F6E742ICR | $82.00 |

Lock

2 Payments

| Procedure Code | Charge Amount | Payment Amount | Adjustment Amount |
|---|---|---|---|
| 71260 | $592.00 | $11.95 | $0.00 |
| 76376 | $82.00 | $1.99 | $0.00 |

Rules Engine  Batch Summary  Batch Summary  Post  Close

FIG. 5(Cont...)

2 Payments

| Charge Amount | Payment Amount | Adjustment Amount | Adjustment type | Approved Amount |
|---|---|---|---|---|
| $592.00 | $11.95 | $0.00 | | $0.00 |
| $82.00 | $1.99 | $0.00 | | $0.00 |

Date of Service: 3/11/2020
Level:
ICN:
Unlock

| Doctor | Date of Service | Procedure | Modifier |
|---|---|---|---|
| 43 - BIRD, BRETT B | 3/11/2020 12:00AM | 76376 - 3D rendering with interpretation and reporting pf computed to | 26 |

○ Teritary None          ○ Other     Insurance

Vehicle$ $0.00   App$ $0.00   Balance$ $0.00   Charge$ $0.00   Rem$ $0.00

Rule Info    Other Payments    Exceptions (8)

ICN         Withhold Adjustment Type

Note

○ Force Hold in Verification    Save

| ID | Patient ID | Exception Message |
|---|---|---|
| 7296964 | 763700 | ERS Payment Mapping Needed |
| 7296968 | 763700 | ERS Payment Mapping Needed |
| 7296966 | 763700 | ERS Payment Mapping Needed |
| 7296972 | 0 | PLB Provider Level Adjustment information included in remittance file, 1 |

Unmapped Payers

FIG. 6(Cont...)

| Insurance Carrier ▼ | Check Number ▼ | Import Date |

| Allowed Amount | Coinsurance Amount | Deduct Amount | Copay Amount |
|---|---|---|---|
| $0.00 | $0.00 | $0.00 | $0.00 |
| $0.00 | $0.00 | $0.00 | $0.00 |

[ Distribute ]  [ Action ▾ ]  [ Copy ]

| Units | Order Number | Charge Amount |
|---|---|---|
| 1.00 | 8B9B4D434F6E742ICR | $82.00 |

◯ Lock

8 Exceptions

| Reason Code | Patient Name | Insurance Carrier |
|---|---|---|
| CO129 | HERRING, HARRIETT H | BCBS - Other |
| CO45 | HERRING, HARRIETT H | MEDICARE |
| CO45 | HERRING, HARRIETT H | MEDICARE |
|  | CHAVEZ, CLARK C | BCBS - Other |

[ Capture Options ] [ Rules Engine ] [ Batch Summary ] [ Bal. Report ] [ Post ] [ Close ]

FIG. 6(Cont...)

SYSTEMS AND METHODS FOR CONCURRENTLY HANDLING MULTIPLE ARTIFACT TYPES IN A UNIFIED GRAPHICAL USER INTERFACE

CROSS-REFERENCE TO RELATED APPLICATIONS

This application claims the benefit of U.S. Provisional Application No. 63/547,983, filed 9 Nov. 2023, which is incorporated in its entirety by this reference.

TECHNICAL FIELD

This invention relates generally to the automated validation and exception management field and, more specifically, to new and useful systems, methods, and user interfaces for concurrently handling multiple artifact types in a unified graphical user interface.

BACKGROUND

Organizations handle a wide variety of artifacts on a daily basis, each requiring validation before being finalized. These artifacts are often grouped into batches for processing. A typical batch may include both validated artifacts—those that have passed the validation process—and exception artifacts, which encounter validation errors due to missing or incorrect information, mismatches, or discrepancies in the provided data.

Exception artifacts necessitate further review and correction, which can be time-consuming and susceptible to human error. On the other hand, validated artifacts, which successfully pass all validation checks without errors, are immediately ready for further processing or finalization.

Managing both exception artifacts and validated artifacts typically requires users to navigate between different interfaces or systems, making it particularly burdensome when dealing with large volumes of artifacts. Accordingly, there is a need for new and useful systems, methods, and user interfaces that enable the concurrent handling of both artifact types in a unified graphical user interface. The embodiments of the present application provide technical solutions to at least address these needs, as well as the deficiencies in the current state of the art.

BRIEF SUMMARY OF THE INVENTION(S)

In some embodiments, a method for concurrently handling multiple artifact types in a unified graphical user interface includes: displaying a multi-artifact handling user interface for concurrently handling a corpus of exception artifacts and a corpus of validated artifacts, wherein the multi-artifact handling user interface includes: a first dynamic artifact user interface component that displays the corpus of exception artifacts in an editable state during a first period, a second dynamic artifact user interface component that displays the corpus of validated artifacts in an un-editable state during the first period, a transition control toggle button that is selectable to transition: the first dynamic artifact user interface component from displaying the corpus of exception artifacts to displaying the corpus of validated artifacts during a second period, and the second dynamic artifact user interface component from displaying the corpus of validated artifacts to displaying the corpus of exception artifacts during the second period, and a plurality of editable user interface elements for modifying a plurality of attributes of an exception artifact selected in the first dynamic artifact user interface component during the first period; detecting an input selecting the transition control toggle button; and based on detecting the input selecting the transition control toggle button: updating the first dynamic artifact user interface component to display the corpus of validated artifacts in the editable state during the second period, updating the second dynamic artifact user interface component to display the corpus of exception artifacts in the un-editable state during the second period, and updating the plurality of editable user interface elements to modify a plurality of attributes of a validated artifact selected in the first dynamic artifact user interface component during the second period.

In some embodiments, a respective editable user interface element of the plurality of editable user interface elements: corresponds to a respective attribute of the plurality of attributes of the exception artifact, includes a value of the respective attribute in the exception artifact, and is visually emphasized to indicate that the value of the respective attribute relates to an exception.

In some embodiments, the method further comprises during the first period: receiving, via the respective editable user interface element, a first input for changing the value of the respective attribute that relates to the exception to a new value that resolves the exception; receiving, via the multi-artifact handling user interface, a second input for modifying, in a computer database, the exception artifact to include the new value of the respective attribute; and based on receiving the first input and the second input: modifying, in the computer database, a record corresponding to the exception artifact to include the new value of the respective attribute that resolves the exception; ceasing display of the exception artifact in the first dynamic artifact user interface element based on the new value of the respective attribute resolving the exception for the exception artifact; converting, in the computer database, the exception artifact to a new validated artifact; and adding the new validated artifact to the second dynamic artifact user interface component.

In some embodiments, during the first period, the first dynamic artifact user interface component includes a table header that indicates: a total number of exception artifacts included in the corpus of exception artifacts, a total value associated with the corpus of exception artifacts, and a total adjustment value associated with the corpus of exception artifacts, and during the second period, the table header of the first dynamic artifact user interface component includes: a total number of validated artifacts included in the corpus of validated artifacts.

In some embodiments, during the first period, the second dynamic artifact user interface includes a table header that includes: the total number of validated artifacts included in the corpus of validated artifacts, and during the second period, the table header of the second dynamic artifact user interface includes: the total number of exception artifacts included in the corpus of exception artifacts, the total value associated with the corpus of exception artifacts, and the total adjustment value associated with the corpus of exception artifacts.

In some embodiments, during the first period, the first dynamic artifact user interface component includes a set of attribute exception columns and a plurality of rows corresponding to the corpus of exception artifacts, and during the second period, the first dynamic artifact user interface component includes a set of validated attribute columns and a plurality of rows corresponding to the corpus of validated artifacts.

In some embodiments, during the first period, the second dynamic artifact user interface component includes a subset of the set of validated attribute columns and the plurality of rows corresponding to the corpus of validated artifacts, and during the second period, the second dynamic artifact user interface component includes a subset of the set of attribute exception columns and the plurality of rows corresponding to the corpus of exception artifacts.

In some embodiments, the multi-artifact handling user interface includes an upper section and a lower section, the upper section of the multi-artifact handling user interface includes the first dynamic artifact user interface component with a width that spans substantially a full width of the upper section, and the lower section includes: the plurality of editable user interface elements with a width that substantially spans from a start of the lower section to a middle of the lower section, and the second dynamic artifact user interface component with a width that substantially spans from the middle of the lower section to an end of the lower section.

In some embodiments, the multi-artifact handling user interface includes an upper section, middle section, and a lower section, the upper section of the multi-artifact handling user interface includes the first dynamic artifact user interface component with a width that spans substantially a full width of the upper section, the middle section of the multi-artifact handling user interface includes the second dynamic artifact user interface component with a width that spans substantially a full width of the middle section, and the lower section includes the plurality of editable user interface elements with a width that substantially spans with a width that spans substantially a full width of the lower section.

In some embodiments, displaying the corpus of exception artifacts in the first dynamic artifact user interface component during the first period includes: displaying the corpus of exception artifacts in association with a set of attribute exception columns, and transitioning, via the transition control toggle button, the second dynamic artifact to displaying the corpus of exception artifacts during the second period includes: displaying the corpus of exception artifacts in association with a subset of the set of attribute exception columns, wherein the subset of the set of attribute exception columns is less than a full size of the set of attribute exception columns.

In some embodiments, the set of attribute exception columns and the subset of the set of attribute exception columns at least includes: an entity identifier column, an exception message column, a reason code column, an entity name column, and a coverage provider column.

In some embodiments, the one or more attribute exception columns included in the set of attribute exception columns that are not included in the subset of the set of attribute exception columns at least comprises: a service date column, a service code column, a service value column, an allocation value column, a record identifier column, and a modification value column.

In some embodiments, the multi-artifact handling user interface further includes an artifact batch selection dialog user interface element comprising a plurality of selection entries corresponding to a plurality artifact validation-exception batches. In some embodiments, the method further comprises: receiving, via the artifact batch selection dialog user interface element, an input selecting a target selection entry of the plurality of selection entries; and based on receiving the input selecting the target selection entry: identifying a respective validation-exception batch of the plurality of artifact validation-exception batches that corresponds to the target selection entry; obtaining, from a computer database, the corpus of exception artifacts associated with the respective validation-exception batch; and obtaining, from the computer database, the corpus of validated artifacts associated with the respective validation-exception batch.

In some embodiments, the exception artifact selected in the first dynamic artifact user interface component during the first period corresponds to a first exception artifact in the corpus of exception artifacts. In some embodiments, the method further comprises: during the first period: receiving, via the first dynamic artifact user interface component, an input for changing the exception artifact selected in the first dynamic artifact user interface component from the first exception artifact to a second exception artifact in the corpus of exception artifacts; and in response to receiving the input for changing the exception artifact selected in the first dynamic artifact user interface component from the first exception artifact to the second exception artifact, updating the plurality of editable user interface elements from modifying the plurality of attributes of the first exception artifact to modifying the plurality of attributes associated with the second exception artifact.

In some embodiments, the validated artifact selected in the first dynamic artifact user interface component during the second period corresponds to a first validated artifact in the corpus of validated artifacts. In some embodiments, the method further comprises: during the second period: receiving, via the first dynamic artifact user interface component, an input for changing the validated artifact selected in the first dynamic artifact user interface component from the first validated artifact to a second validated artifact in the corpus of validated artifacts; and in response to receiving the input for changing the validated artifact selected in the first dynamic artifact user interface component from the first validated artifact to the second validated artifact, updating the plurality of editable user interface elements from modifying the plurality of attributes of the first validated artifact to modifying the plurality of attributes associated with the second validated artifact.

In some embodiments, displaying the corpus of validated artifacts in the second dynamic artifact user interface component during the first period includes: displaying the corpus of validated artifacts in association with a set of validated attribute columns, and transitioning, via the transition control toggle button, the first dynamic artifact to displaying the corpus of validated artifacts during the second period includes: displaying the corpus of validated artifacts in association with a superset of validated attribute columns, wherein the superset of validated attribute columns includes the set of validated attribute columns.

In some embodiments, the set and superset of validated attribute columns at least includes: an entity identifier column, a coverage provider column, a service date column, a service code column, an allocation value column, and a modification value column.

In some embodiments, one or more validated attribute columns included in the superset of validated attribute columns that are not included in the set of validated attribute columns at least comprises: a modification type column, a permitted value column, a shared responsibility value column, an initial requirement value column, and a fixed contribution amount column.

In some embodiments, a computer-program product comprises a non-transitory machine-readable storage medium storing computer instructions that, when executed by one or more processors, perform operations comprising: displaying a multi-artifact handling user interface for concurrently handling a corpus of exception artifacts and a corpus of validated artifacts, wherein the multi-artifact handling user interface includes: a first dynamic artifact user interface component that displays the corpus of exception artifacts in an editable state during a first period, a second dynamic artifact user interface component that displays the corpus of validated artifacts in an un-editable state during the first period, a transition control toggle button that is selectable to transition: the first dynamic artifact user interface component from displaying the corpus of exception artifacts to displaying the corpus of validated artifacts during a second period, and the second dynamic artifact user interface component from displaying the corpus of validated artifacts to displaying the corpus of exception artifacts during the second period, and a plurality of editable user interface elements for modifying a plurality of attributes of an exception artifact selected in the first dynamic artifact user interface component during the first period; detecting an input selecting the transition control toggle button; and based on detecting the input selecting the transition control toggle button: updating the first dynamic artifact user interface component to display the corpus of validated artifacts in the editable state during the second period, updating the second dynamic artifact user interface component to display the corpus of exception artifacts in the un-editable state during the second period, and updating the plurality of editable user interface elements to modify a plurality of attributes of a validated artifact selected in the first dynamic artifact user interface component during the second period.

In some embodiments, a computer-implemented system comprises: one or more processors; a memory; and a computer-readable medium operably coupled to the one or more processors, the computer-readable medium having computer-readable instructions stored thereon that, when executed by the one or more processors, cause a computing device to perform operations comprising: displaying a multi-artifact handling user interface for concurrently handling a corpus of exception artifacts and a corpus of validated artifacts, wherein the multi-artifact handling user interface includes: a first dynamic artifact user interface component that displays the corpus of exception artifacts in an editable state during a first period, a second dynamic artifact user interface component that displays the corpus of validated artifacts in an un-editable state during the first period, a transition control toggle button that is selectable to transition: the first dynamic artifact user interface component from displaying the corpus of exception artifacts to displaying the corpus of validated artifacts during a second period, and the second dynamic artifact user interface component from displaying the corpus of validated artifacts to displaying the corpus of exception artifacts during the second period, and a plurality of editable user interface elements for modifying a plurality of attributes of an exception artifact selected in the first dynamic artifact user interface component during the first period; detecting an input selecting the transition control toggle button; and based on detecting the input selecting the transition control toggle button: updating the first dynamic artifact user interface component to display the corpus of validated artifacts in the editable state during the second period, updating the second dynamic artifact user interface component to display the corpus of exception artifacts in the un-editable state during the second period, and updating the plurality of editable user interface elements to modify a plurality of attributes of a validated artifact selected in the first dynamic artifact user interface component during the second period.

BRIEF DESCRIPTION OF THE FIGURES

FIG. 2 illustrates an example method 200 in accordance with one or more embodiments of the present application; and FIGS. 3-6 illustrates examples of an integrated artifact management user interface in accordance with one or more embodiments of the present application.

DESCRIPTION OF THE PREFERRED EMBODIMENTS

The following description of the preferred embodiments of the invention is not intended to limit the invention to these preferred embodiments, but rather to enable any person skilled in the art to make and use this invention.

Figure 1:
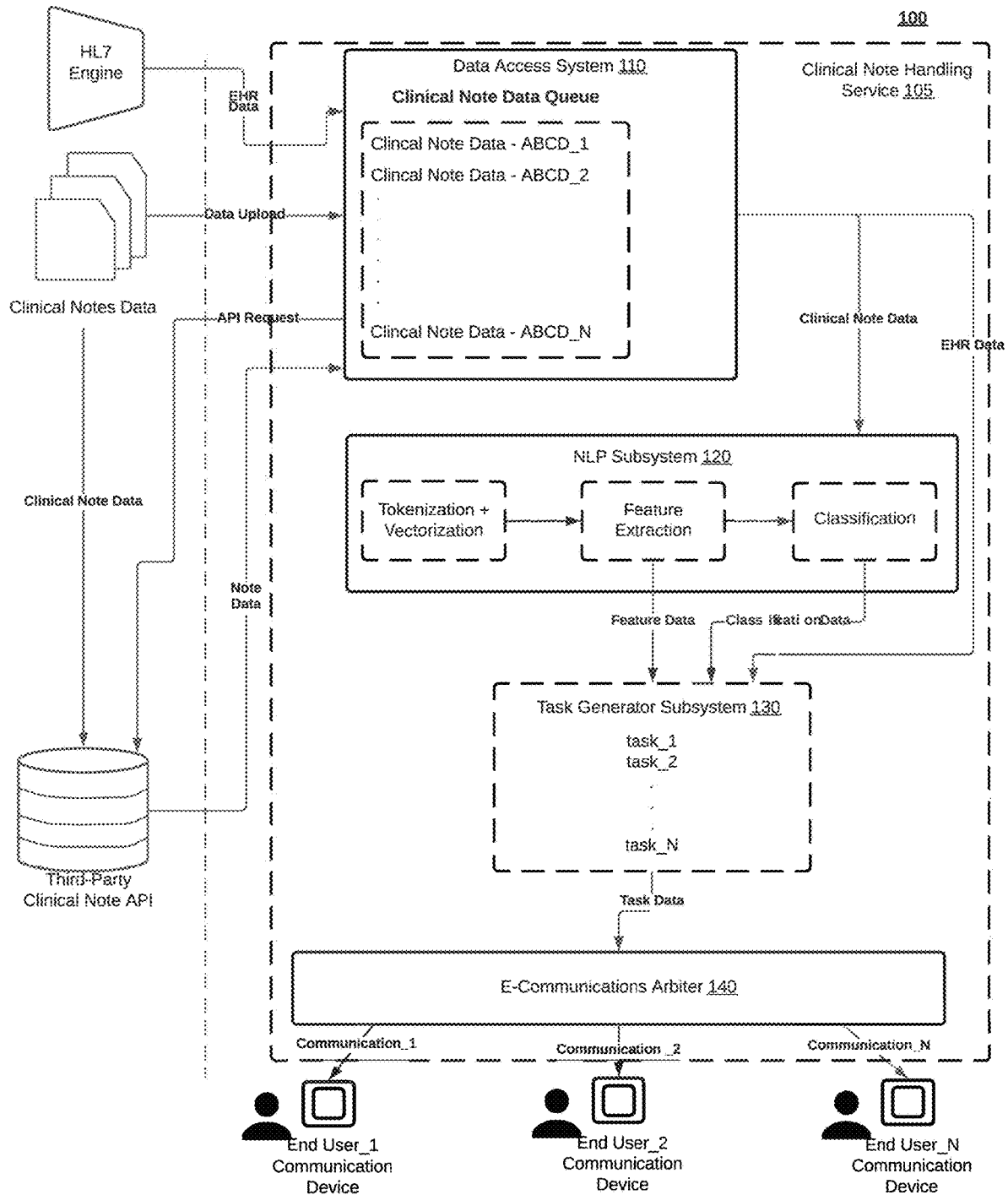
FIG. 1 illustrates a schematic representation of a system 100 in accordance with one or more embodiments of the present application.
Figure 1A:
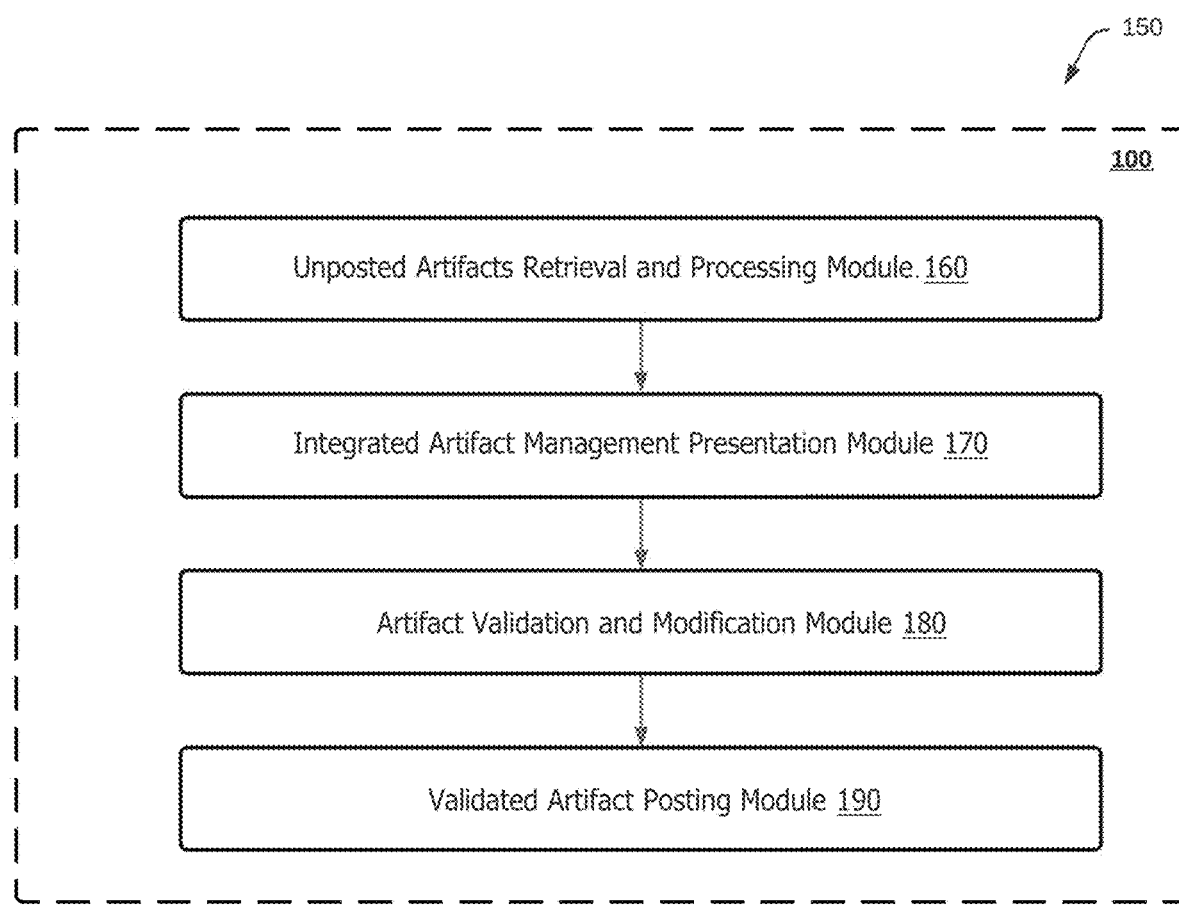
FIG. 1A illustrates a schematic representation of a subsystem 150 of the system 100 in accordance with one or more embodiments of the present application.

1. Medical Data Processing System with Embedded Discrepancy Resolution and Validation Protocols As shown in FIGS. 1 and 1A, a medical data processing system 100 with embedded discrepancy resolution and validation protocols may include a clinical note handling service 105 and a unified artifact and exception management subsystem 150. The service 105 and the subsystem 150 may each be configured to perform specific functions within the system 100 and may operate independently of or in conjunction with one another. It shall be noted that while FIGS. 1 and 1A illustrate the system 100 as including both the clinical note handing service 105 and the unified artifact and exception management subsystem 150, other embodiments of the system 100 may only include one of these two components (or include other modules not explicitly depicted in FIGS. 1 and 1A).

The clinical note handling service 105, as illustrated in FIG. 1, may include a clinical note data access and intake subsystem 110, a feature extraction and classification subsystem 120, an automated task generation subsystem 130, and an electronic communications subsystem 140. Conversely, as shown in FIG. 1A, the unified artifact and exception management subsystem 150 may include an unposted artifacts retrieval and processing module 160, an integrated artifact and exception management presentation module 170, an artifact validation and modification module 180, and a validated artifact posting module 190.

1.05 Clinical Note Data Handling and Automated Electronic Communications Service The clinical note data handling and automated electronic communications service 105 implementing the system 100, sometimes referred to herein as the "clinical note handling service 105" may be implemented by a distributed network of computers (e.g., hosted on the cloud, etc.) and may be in operable and control communication with each of the subsystems of the system 100 and/or third-party subsystems and services. That is, the clinical note handling service 105 may include a centralized controlling computer server(s) and associated computing systems that encourages and/or controls the intelligent and accelerated clinical note data handling, clinical note data classification, and clinical note data-informed communications routing operations of each of the subsystems, described herein, (e.g., subsystems 110-140).

1.1 Clinical Note Data Access+Intake Subsystem

The clinical note data access and intake subsystem no, which may be sometimes referred to herein as the "data access system" 110, preferably functions to enable one or more electronic connections between the system 100 and one or more external systems of one or more subscribers to the clinical note handling service 105. The data access subsystem 110 may include one or more access modules that may function to establish or create content communication channels, which are sometimes referred to as "data handling nexus", between the system 100 and systems associated with subscribers to the service 105. In one or more embodiments, the data handling nexus may include any suitable medium and/or method of transmitting digital items between at least two devices including, but not limited to, a service bus, a digital communication channel or line, and/or the like.

Additionally, or alternatively, the clinical note data access and intake subsystem 110 may provide a web-based graphical user interface or web application that may enable one or more subscribers to upload clinical note data (e.g., clinical note CSV files, and/or the like) directly into the system 100.

In one or more embodiments, based on accessing or receiving clinical note data, the data access system 110 may function to store the clinical note data in a queue and preferably generate and/or associate identifying metadata including, but not limited to, a session identifier providing a unique identification value for a clinical session associated with a target clinical note, a patient identifier, a doctor identifier, a clinical note identifier, and/or the like. In such embodiments, the identifying metadata may be passed along with the clinical note data to one or more downstream subsystems (e.g., subsystem 120, subsystem 130, subsystem 140) to enable processing, tracking, account identification, and/or the like.

In one or more embodiments, the clinical note data handling service 105 may function to implement a clinical note data handling application programming interface (API) that enables programmatic communication, access, and control between the system 100 and the one or more subservices within the system 100 and one or more (third-party) APIs associated with one or more subscribers to the clinical note data handling service 105.

Additionally, or alternatively, the data access system 110 may receive the clinical notes data via a health level seven (HL7) interface. In such embodiments, an electronic health record (EHR) system associated with a subscriber may periodically or in real-time send one or more HL7 messages comprising clinical note data and/or other types of electronic health record (EHR) data to the data access system 110. In turn, the data access system no may receive the one or more HL7 messages via a secure channel (e.g., port) of the clinical note handling service 105 and provide the one or more HL7 messages to the NLP subsystem 120.

1.2 NLP: Feature Identification+Extraction and Classification Subsystem

The feature extraction and classification subsystem 120, which may sometimes be referred to herein as a "NLP subsystem", preferably functions to perform various natural language processing tasks including extracting features from clinical note data and computing one or more classification inferences and/or labels for each clinical note file being handled by the clinical note data handling service 105. The NLP subsystem 120 may additionally include one or more text processing modules and/or machine learning models that may tokenize textual data within a clinical note and vectorize and/or generate embeddings for each set of tokens and further cluster the tokens into semantically related token groups or the like.

In one or more embodiments, the NLP subsystem 120 includes a machine learning module or subsystem that may be intelligently configured to predict various classifications for each clinical note document including, but not limited to, identifying whether a clinical note has a clinical recommendation, a number of clinical recommendations in a given clinical note, a type of clinical recommendation, a strength of a clinical recommendation, an urgency of a clinical recommendation, and/or the like. In such embodiments, the NLP subsystem 120 may include a plurality of distinct machine learning-based classification submodules, which may be outlined herein below in the method 200.

Additionally, or alternatively, in some embodiments, the NLP subsystem 120 may include extensible feature extraction and classification heuristics that may be applied alone or in combination with one or more machine learning-based classifiers described herein.

Additionally, or alternatively, the NLP subsystem 120 may implement one or more ensembles of pre-trained or trained machine learning models. The one or more ensembles of machine learning models may employ any suitable machine learning including one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), adversarial learning, and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, density-based spatial clustering of applications with noise (DBSCAN), expectation maximization, etc.), a bidirectional encoder representation form transformers (BERT) for masked language model tasks and next sentence prediction tasks and the like, variations of BERT (i.e., ULMFiT, XLM UDify, MT-DNN, SpanBERT, RoBERTa, XLNet, ERNIE, KnowBERT, VideoBERT, ERNIE BERT-wwm, MobileBERT, TinyBERT, GPT, GPT-2, GPT-3, GPT-4 (and all subsequent iterations), ELMo, content2Vec, and the like), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and any suitable form of machine learning algorithm. Each processing portion of the system 100 can additionally or alternatively leverage: a probabilistic module, heuristic module, deterministic module, or any other suitable module leveraging any other suitable computation method, machine learning method or combination thereof. However, any suitable machine learning approach can otherwise be incorporated in the system 100. Further, any suitable model (e.g., machine learning, non-machine learning, etc.) may be implemented in the various systems and/or methods described herein.

1.3 Automated Recommendation Task Generator

The automated recommendation handling task and instructions generator 130, which may be sometimes referred to herein as a "tasks generator" 130 or "automated task generation subsystem" 130, preferably functions to automatically generate a clinical recommendation registry including one or more tasks and/or one or more instructions for handling and/or disposing of clinical recommendations identified within a clinical note. In one or more embodiments, the task generator 130 may take in as input a set of extracted features and a set of classification inferences computed by the NLP subsystem 120 to compose and/or structure a given registry. It shall be noted that, in some portions of the disclosure, a "clinical recommendation registry" may be referred to as a "clinical recommendation worklist" or the like.

A given clinical recommendation registry preferably includes an enumeration of tasks and/or computer-executable instructions that may be automatically executed by the clinical note handling service 105. Additionally, or alternatively, the clinical recommendation registry may include patient session identifier (ID) data, clinical recommendation ID data, patient communications account data (e.g., email, phone number, messaging ID, etc.) that may be used as input in structuring one or more electronic communications to a given patient, as described herein and using at least e-communications arbiter 140.

Furthermore, in some embodiments, the task generator 130 may also be capable of ingesting additional electronic health record (EHR) data, such as appointment data, discharge data, transfer data, prescription data, and/or the like. This additional data may inform one or more operations of the task generator 130 and/or may be directly or indirectly provided as input to the e-communications arbiter 140 for structuring electronic communications to a given patient or other end users (e.g., a referring doctor, care team, etc.).

1.4 Automated E-Communications Arbiter & Routing

The electronic communications subsystem 140, which may be sometimes referred to herein as an "e-communications arbiter" 140, preferably functions to take in as input a clinical recommendation registry associated with a target clinical recommendation and structure, as output, an automated electronic communication scheme for handling and/or disposing of the target clinical recommendation. Accordingly, the e-communications arbiter 140 may function to intelligently select an optimal communication channel for communicating with an end user or patient, structuring communication parameters, such as a communication schedule and/or communication frequency and composing message content for each communication to the end user. In one or more embodiments, the e-communication arbiter may function to employ a selection matrix or the like for selecting a most optimal communication channel and may further employ pre-trained language models and/or messaging templates to compose messaging content for a given communication.

1.5 Unified Artifact Management Subsystem

The unified artifact management subsystem 150 may operate to display an integrated (e.g., unified) artifact management user interface. The operations performed by the integrated artifact management user interface may be executed or supported via one or more of the sub-modules illustrated in FIG. 1A. As illustrated in FIG. 1A, the unified artifact management subsystem 150 may comprise one or more modules 160-190 that are each configured to perform distinct functions. Some of the functions performed by each of the sub-modules 160-190 will now be described below and in greater detail in the method 200.

In some embodiments, the unposted artifacts retrieval and processing module 160 may function to retrieve a set of unposted artifacts. The set of unposted artifacts may be obtained from a variety of data sources, such as a database storing artifact data. To extract the set of unposted artifacts from the database, a specific query may be constructed and executed. This query may be constructed based on various parameters such as transaction date, transaction type, payer details, artifact status, insurance carrier, check number, batch number, artifact ID, and/or any other relevant transaction attribute. Once the unposted artifacts retrieval and processing module 160 executes the query and the set of unposted artifacts are received, the module 160 may process such a set of unposted artifacts for display within the integrated artifact management user interface.

The integrated artifact management presentation module 170, in some embodiments, may function to render the artifact exceptions and validated artifacts associated with the selected set of unposted artifacts. Specifically, the module 170 may present the artifact exceptions and validated artifacts in separate grids or tables within the integrated artifact management user interface. Each grid may include various columns representing different attributes of the transactions, such as transaction date, transaction amount, payer details, patient details, artifact status, and any identified exceptions or discrepancies.

In some embodiments, the module 170 may be configured to detect when a user selects one of the validated artifacts or artifact exceptions being displayed in the integrated artifact management user interface. Based on the module 170 detecting a user selection of a respective validated artifact or artifact exception, the module 170 may respond by highlighting the selected artifact and by presenting additional details (e.g., attributes or properties) of the selected artifact. This may include displaying more detailed information about the selected artifact, providing options for editing the selected artifact, or initiating a process for resolving any identified exceptions.

In some embodiments, the artifact validation and modification module 180 may be configured to save and validate user modifications made to one or more (previously) validated artifacts and/or one or more artifact exceptions. Prior to saving the user modifications to a database or the like, the module 180 may initiate a validation process that includes applying a set of predefined validation rules to the modified artifacts. If any discrepancies or errors are identified during the validation process, the module 180 may flag these artifacts and alert the user of potential issues that may require further review or correction. Conversely, if the modified artifacts pass the validation process, these artifacts may be marked as validated, signifying that they are ready for further processing or posting.

In some embodiments, the validated artifact posting module 190 may be configured to handle the posting of one or more validated artifacts. The operations of the module 190 may be triggered based on a user request to post one or more validated artifacts to corresponding patient accounts. Upon a successful posting of one or more validated artifacts, the module 190 may update the status of the one or more validated from a 'validated' state to a 'posted' state to indicate to the user that the one or more validated artifacts have been successfully posted and applied to a corresponding patient account.

2.0 Method for Concurrent Handling of Multiple Artifact Types

As shown in FIG. 2, a method 200 for concurrent handling of multiple artifact types may include identifying, via a user interface, a set of unposted artifacts (S210), modifying, via the user interface, at least one artifact (or artifact exception) in the set of unposted artifacts (S220), re-validating the modified validated artifacts or artifact exceptions (S230), and posting the validated artifacts (S240).

The method for concurrent handling of multiple artifact types, as described herein, may offer significant technical advantages over challenges often encountered in artifact validation and management systems, including introducing a unified graphical user interface (GUI) that enables users to manage both validated and exception artifacts simultaneously. Managing both exception artifacts and validated artifacts typically requires users to navigate between different interfaces or systems, which can be particularly burdensome when handling large volumes of artifacts. The embodiments of the present application provide technical solutions to at least address these needs and improve upon deficiencies in the current state of the art.

Furthermore, by integrating and dynamically updating validated artifacts and artifact exceptions within a single interface, the method may enable concurrent operations on various artifact types without necessitating separate interfaces or extensive re-validation steps. This may reduce processing time and may help maintain consistency across artifact records, potentially enhancing system reliability and user efficiency.

Another technical advantage of method 200 may include real-time responsiveness of the integrated artifact management interface, which may adapt dynamically as artifacts transition between validation states. This may allow for artifacts' statuses to remain accurately reflected in the interface, promoting more seamless artifact management and potentially reducing processing errors. Additionally, by displaying artifact exceptions and validated artifacts in either editable or uneditable states based on their validation status, the method may minimize redundant user interactions and support efficient error resolution.

Additionally, the method's ability to apply validation rules automatically upon user modification of an artifact, with immediate state updates in the interface, may also be beneficial for incorporating an automated feedback loop that streamlines the artifact verification process. This capability may reduce the cognitive load on users by guiding them through the validation workflow, potentially enhancing system usability and productivity.

Moreover, the inclusion of customizable filter fields and toggle controls within the interface may allow for tailored data views, enabling users to focus on relevant artifacts or validation-exception batches. This flexibility in artifact handling may reduce the time required to locate specific records, promoting a more streamlined and efficient artifact processing workflow.

2.10 Identifying a Set of Unposted Artifacts (e.g., an Artifact Validation-Exception Batch)

S210, which includes identifying a set of unposted artifacts, may function to obtain or retrieve a set of unposted artifacts for display within an integrated artifact management user interface (sometimes referred to herein as a multi-artifact handling user interface). As will be described in more detail herein, based on the identification (or selection) of the set of unposted artifacts, S210 may function to dynamically update the integrated artifact management user interface with one or more artifact exceptions and/or one or more validated artifacts underlying such set of unposted artifacts.

In some embodiments, the one or more artifact exceptions included in the set of unposted artifacts may be referred to as a corpus of exception artifacts and/or may relate to artifacts that have encountered validation issues during an artifact validation process. It shall be noted that such validation issues may arise or surface for various reasons such as mismatched information, incorrect details, discrepancies in the artifact attributes, and/or the like. Conversely, in some embodiments, the one or more validated artifacts included in the set of unposted artifacts may be referred to as a corpus of validated artifacts and/or may relate to artifacts that have successfully passed the artifact validation process and are ready to be posted to corresponding user accounts (e.g., patient accounts).

ERS Batch Number Input Element

Figure 3:
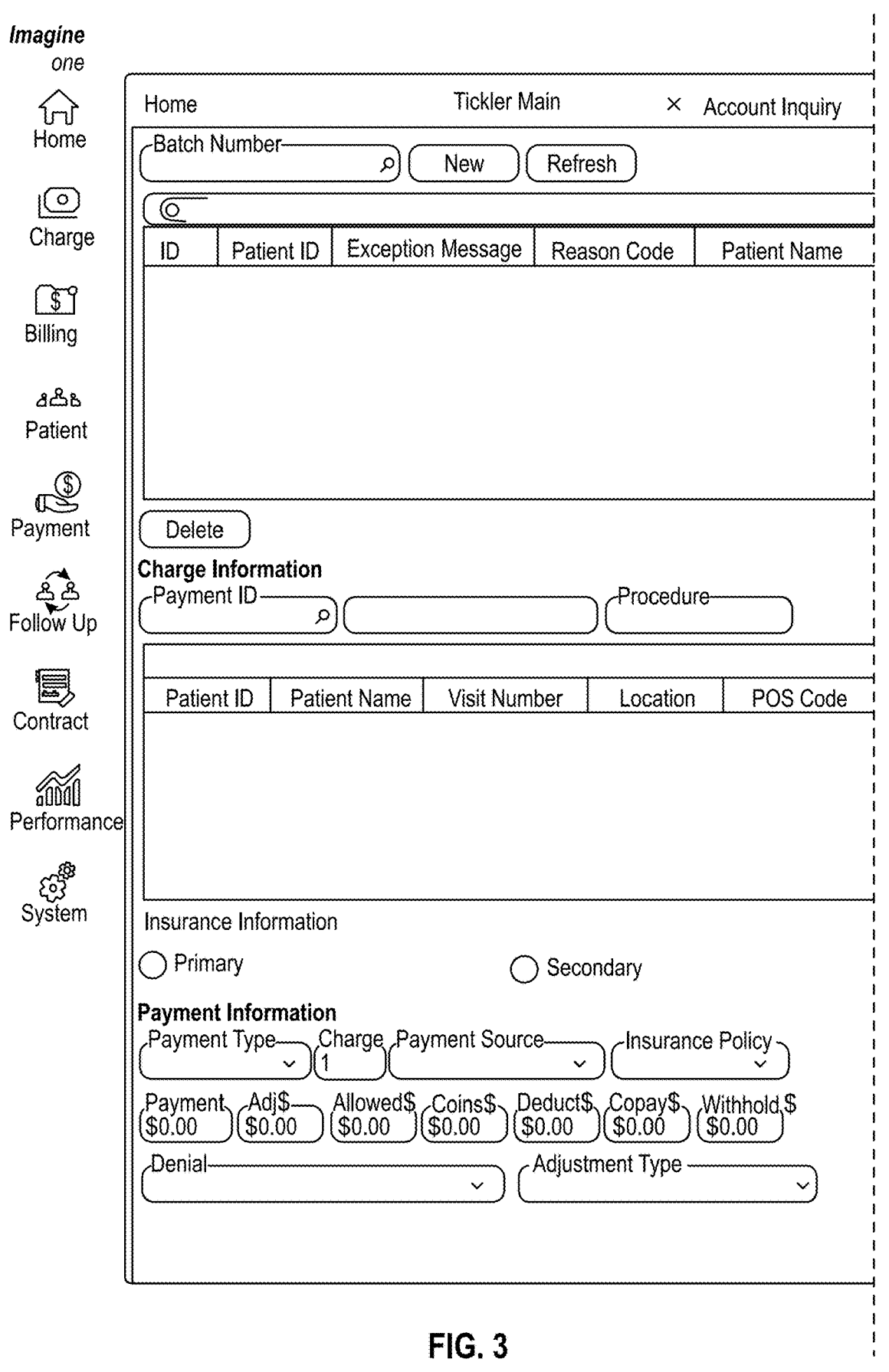
Figure 3:
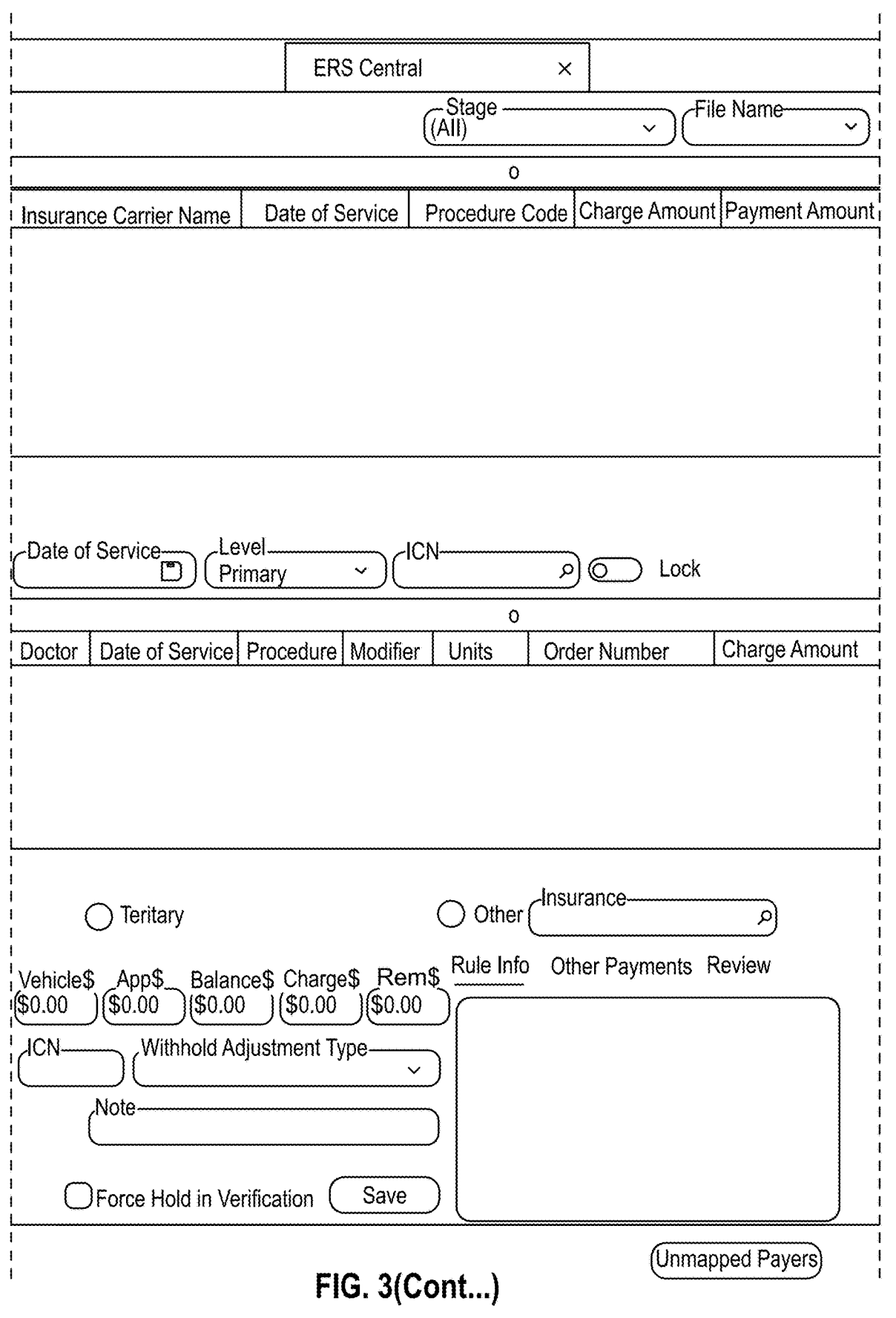
Figure 3:
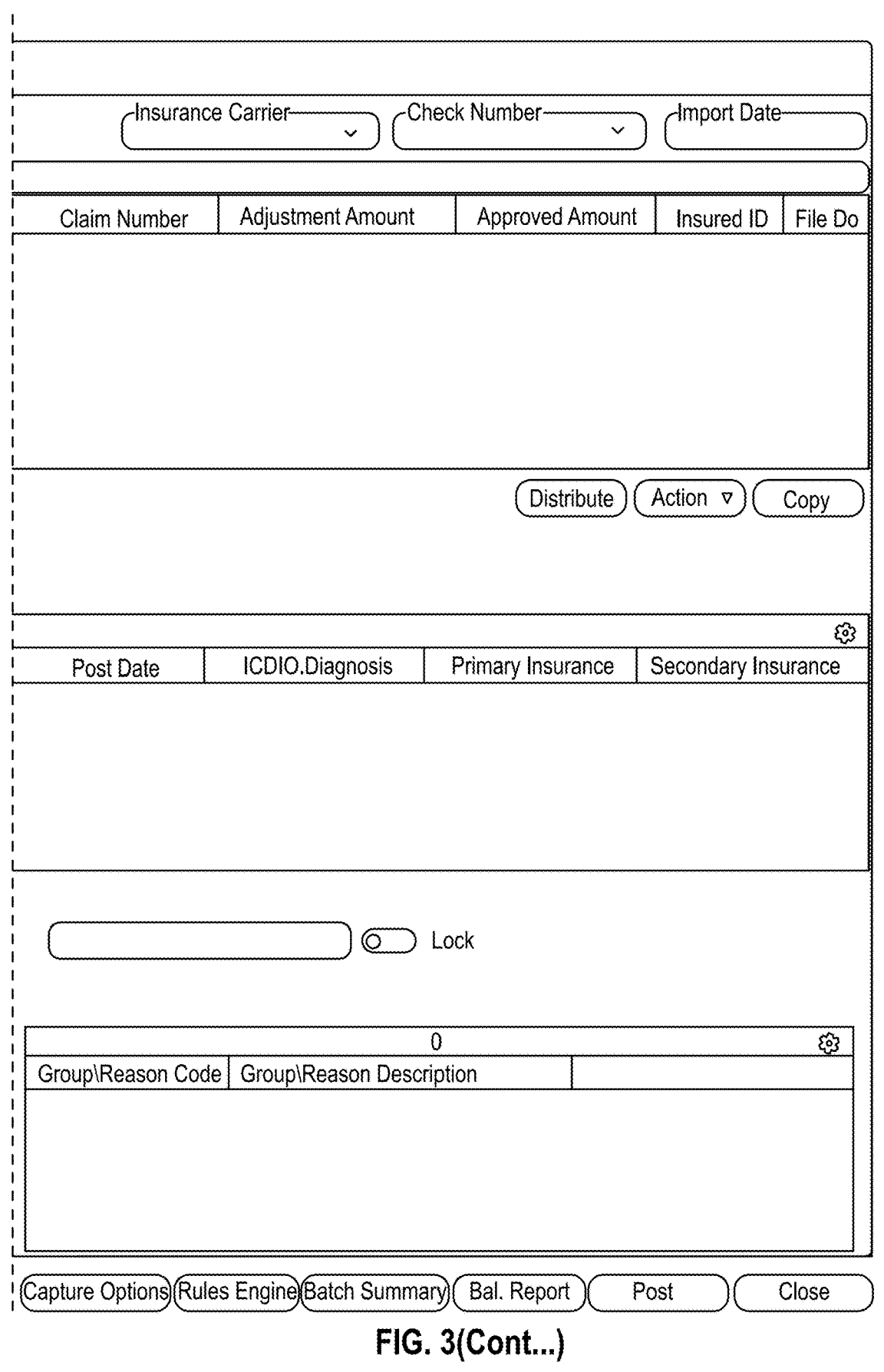

In some embodiments, the integrated artifact management user interface may include a selectable user interface element that allows a user to select or specify a particular set of unposted artifacts for review and processing. An example of such a user interface element is illustrated in FIG. 3. Specifically, in FIG. 3, the batch number input user interface element may be configured to receive an input of a user-provided evaluated receipt settlement (ERS) batch number (e.g., an identifier of a respective artifact validation-exception batch). Additionally, or alternatively, in some embodiments, the batch number input user interface element (or at least a portion thereof) may be selectable for displaying a list of available ERS batch numbers, as generally illustrated in FIG. 4.

It shall be noted that, in some portions of the disclosure, "a set of unposted artifacts" (or similar recitations) may be individually referred to as "an evaluated receipt settlement (ERS) batch or batch number," "an artifact validation-exception batch," or any other suitable term that represents a group of artifacts that have been received but not yet posted or settled (e.g., to user accounts). Similarly, it shall also be noted that, in some portions of the disclosure, multiple sets of unposted artifacts may be collectively referred to as "a plurality of evaluated receipt settlement (ERS) batches or batch numbers," "a plurality of artifact validation-exception batches," or any other suitable term that represents groups of artifacts that have been received but not yet posted or settled (e.g., to user accounts).

ERS Batch Number Selection Dialog

An example user interface that S210 may display in response to detecting a user request to display a list of Unposted ERS batch numbers is illustrated in FIG. 4. Specifically, in FIG. 4, S210 is displaying an ERS batch number selection dialog, sometimes referred to as an artifact batch selection dialog user interface element, overlaid on the integrated artifact management user interface. Furthermore, as also illustrated in FIG. 4, the ERS batch number selection dialog may include various user interface components including, but not limited to, an ERS batch filter component and/or a list of unposted ERS batch numbers. The ERS filter component, in some embodiments, may be configured to filter (e.g., tailor) the list of unposted ERS batch numbers based on a variety of user-specified filter conditions or criteria. It shall be noted that in embodiments where the ERS filter component does not have any filter conditions specified, the list of unposted ERS batch numbers displayed within the selection dialog may include all available unposted ERS batch numbers.

In some embodiments, the ERS filter component may include one or more filter fields that each perform a respective filter functionality. The one or more filter fields may include, but should not be limited to, a batch number filter field, an insurance carrier filter field, a check number filter field, a patient or recipient identification (ID) filter field, and/or the like. The batch number filter field may be configured to accept or receive user input comprising a specific batch number and, in turn, cause S210 to filter the list of unposted ERS batch numbers to only include ERS batch numbers matching the received user input.

Conversely, the insurance carrier filter field may be configured to receive or accept user input comprising a name of a specific insurance carrier and, in turn, cause S210 to filter the list of unposted ERS batch numbers to only include ERS batch numbers matching the specific insurance carrier specified by the user input. Furthermore, the check number filter field may be configured to receive or accept a user input comprising a check number and, in turn, cause S210 to filter the list of unposted ERS batch numbers to only include ERS batch numbers matching the check number specified by the user input. Lastly, the patient or recipient identification (ID) filter field may be configured to receive or accept a user input comprising a patient ID and, in turn, cause S210 to filter the list of unposted ERS batch numbers to only include ERS batch numbers relating to the patient or recipient ID specified in the user input.

It shall be noted that, in operation, the above-described ERS batch number filter fields may enable a user to efficiently locate ERS batch numbers that align with specific characteristics, attributes, or properties that are of interest to the user. Thus, time spent searching for relevant ERS batches as well as the overall search burden on the user may be significantly reduced.

In some embodiments, the ERS batch number selection dialog may present the list of unposted ERS batch numbers in a tabular format. When displayed in a tabular format, the list of unposted ERS batch numbers may comprise one or more rows and one or more columns. The one or more rows, sometimes referred to as one or more selection entries, may each correspond to a distinct ERS batch number and the one or more columns may each be configured to store a specific property or attribute of the distinct ERS batch number. For instance, as illustrated in FIG. 4, displaying the list of unposted ERS batch numbers in the tabular format may include displaying a batch number column, a minimum import date column, a maximum import date column, an artifact count column, and/or a plurality of ERS batch number rows. The batch number column, the minimum import date column, the maximum import date column, and the count column may display the batch number, the earliest date of import, the latest date of import, and the total number of artifacts associated with each ERS batch number row, respectively.

Selecting & Displaying an Unposted ERS Batch Number

In some embodiments, while displaying the ERS batch number selection dialog, S210 may function to receive one or more inputs that select a respective ERS batch number from the list of unposted ERS batch numbers. The one or more inputs may be provided by the user via various means and/or methods, such as clicking on a desired (e.g., target) ERS batch number row, using keyboard navigation to highlight and select the desired ERS batch number row, or touching the desired batch number row if the user interface is being accessed on a touch screen device. Additionally, in some embodiments, the one or more inputs received by S210 may include a selection of a "Select" or "Confirm" button while the desired ERS batch number row is selected or highlighted. Such input, while optional in some embodiments, may signify to S210 that the user is confirming or finalizing their selection of the ERS batch number row and is requesting that the one or more validated artifacts and artifact exceptions underlying the currently selected ERS batch number row be displayed on the integrated artifact management user interface.

In some embodiments, based on receiving the aforementioned input(s), S210 may function to dynamically update one or more components or elements displayed in the integrated artifact management user interface. The one or more components or elements updated by S210 may include, but should not be limited to, a validated artifact grid component and/or an artifact exceptions grid component. It shall be noted that, in some portions of the disclosure, the term "validated artifact grid" may be interchangeably referred to as an "artifacts table," a second dynamic artifact user interface component," or similar recitations, and the "artifact exceptions grid" may be interchangeably referred to as an "exceptions table," "a second dynamic artifact user interface component," or similar recitations.

An example of S210 updating the integrated artifact management user interface based on the input(s) detected in FIG. 4 is illustrated in FIG. 5. Specifically, as shown in FIG. 5, S210 may dynamically update (e.g., load) the artifact exceptions associated with the ERS batch number selected in FIG. 4 into the artifact exceptions grid and/or may dynamically update (e.g., load) the validated artifacts associated with the ERS batch number selected in FIG. 4 into the validated artifacts grid. It shall be noted that the above example is not intended to be limiting and that if S210 detected input(s) selecting a different ERS batch number row in FIG. 4, S210 may instead dynamically update the artifact exceptions grid and the validated artifacts grid with the artifact exceptions and validated artifacts associated with the different ERS batch number row.

Additionally, in some embodiments, based on receiving the aforementioned input(s) selecting the target selection entry, S210 may identify a respective validation-exception batch from a plurality of artifact validation-exception batches that corresponds to the target selection entry. For example, if the selected entry corresponds to a specific ERS batch number, S210 may analyze the metadata associated with that batch number to identify the correct validation-exception batch that holds both the artifact exceptions and validated artifacts linked to that ERS batch. Thus, once the selected validation-exception batch is identified, S210 may obtain, from a computer database, the corpus of exception artifacts associated with the identified validation-exception batch. Furthermore, in some embodiments, S210 may obtain, from the same or another computer database, the corpus of validated artifacts that are associated with the identified validation-exception batch.

Additionally, as illustrated in FIG. 5, the validated artifacts grid and the artifact exceptions grid may be arranged in a tabular format comprising one or more rows and one or more columns (sometimes referred to as attribute exception columns). The one or more rows in the exceptions grid may each correspond to and include exception attribute values of a distinct artifact exception underlying the selected (or specified) ERS batch number. Conversely, the one or more columns in the exceptions grid may each represent a particular attribute or property of an artifact exception, such as an exception identification (ID) column (sometimes referred to as a record identifier column), a patient or recipient identification (ID) column (sometimes referred to as an entity identifier column), an exception message column, a reason code column, a patient or recipient name column (sometimes referred to as an entity name column), an insurance carrier name column (sometimes referred to as a coverage provider column), a date of service column (sometimes referred to as a service date column), a procedure code column (sometimes referred to as a service code column), a charge amount column (sometimes referred to as an allocation value column), an artifact amount column, a claim number column, an adjustment amount (sometimes referred to as a modification value column), and/or the like.

Furthermore, as also illustrated in FIG. 5, the one or more rows in the validated artifacts grid may each correspond to and include validated attribute values of a distinct validated artifact underlying the selected (or specified) ERS batch number. Conversely, the one or more columns in the validated artifacts grid (sometimes referred to as validated attribute columns) may each represent a particular attribute or property of a validated artifact, such as a patient or recipient identification (ID) column (sometimes referred to as an entity identifier column), an insurance carrier name column (sometimes referred to as a coverage provider column), a service date column, a procedure code column (sometimes referred to as a service code column), a charge amount column (sometimes referred to as an allocation value column), an artifact amount column, an adjustment amount column (sometimes referred to as a modification value column), an adjustment type column (sometimes referred to as a modification type column), an approved amount column, an allowed amount column (e.g., a permitted value column), a coinsurance amount column (sometimes referred to as a fixed contribution amount column), a deductible amount column, the copay amount (sometimes referred to as an initial requirement value column), and/or the like.

2.20 Modifying at Least One Artifact within the Set of Unposted Artifacts

S220, which includes modifying at least one artifact, may function to receive user input(s) for modifying one or more artifacts displayed in the integrated artifact management user interface. A result of modifying the one or more artifacts in the manner described herein may include attributes or properties of the modified artifacts being updated to new value(s) according to the inputs obtained from the user. For example, in a non-limiting example, S220 may receive user inputs for updating or changing an artifact amount attribute, payer information attribute, a artifact method attribute and/or the like of a target artifact. In turn, based on this input, S220 may update the target artifact from a previous state (e.g., exception state) to a new state (e.g., valid state) that reflects the user inputs.

Updating an Artifact Exception

In some embodiments, modifying at least one artifact may include modifying one or more artifact exceptions displayed in the integrated artifact management user interface. Generally, a respective artifact exception may be modified upon S220 receiving a user input selecting the respective artifact exception in the artifact exceptions grid and one or more user inputs for modifying attributes or properties of the currently selected artifact exception. In turn, based on receiving the user input(s), S220 may function to update the attributes or properties of the selected artifact exception in accordance with the user input(s) and save the modified artifact exception to a database (e.g., a computer database) storing a plurality of artifact exceptions. It shall be noted that, in some embodiments, the saving of the modified artifact exception may occur upon S220 receiving a user input for saving the modified artifact exception (e.g., selecting the "Save" button illustrated in FIG. 5).

It shall also be noted that in embodiments where the artifact exceptions are selectable for modification (e.g., they are being displayed in the first dynamic artifact user interface component), this may be referred to as displaying the artifact exceptions in an editable state. Conversely, if the artifact exceptions are not selectable for modification (e.g., they are being displayed in the second dynamic artifact user interface component), this may be referred to as displaying the artifact exceptions in an un-editable state.

In some embodiments, upon detecting a selection of an artifact exception, S220 may update a plurality of editable user interface elements of the integrated artifact management user interface to display details (e.g., attribute values or property values) of the selected artifact exception. For instance, as shown by way in FIG. 5, based on or in response to S220 receiving user input selecting the artifact exception corresponding to ID #7296968, S220 may visually emphasize (e.g., highlight) such artifact exception in the artifact exceptions grid to indicate the artifact exception currently selected for modification and/or may further update an artifact information section of the integrated artifact management user interface with attribute values and/or property values of the selected artifact exception.

In some embodiments, as illustrated in FIG. 5, the attributes and properties displayed in the artifact information section may include, but should not be limited to, the artifact type associated with the selected artifact exception, the charge amount associated with the selected artifact exception, the artifact source associated with the selected artifact exception, the insurance policy associated with the selected artifact exception, the variance amount associated with the selected artifact exception, the approximate amount associated with the selected artifact exception, the balance amount associated with the selected artifact exception, the charge amount associated with the selected artifact exception, the remittance amount associated with the selected artifact exception, the artifact amount associated with the selected artifact exception, the adjusted amount associated with the selected artifact exception, the allowed amount associated with the selected artifact exception, the co-insurance amount associated with the selected artifact exception, the copay amount associated with the selected artifact exception, the withholding amount associated with the selected artifact exception, the ICN code associated with the selected artifact exception, the withholding adjustment type associated with the selected artifact exception, the denial reason associated with the selected artifact exception, the adjustment type associated with the selected artifact exception, the notes associated with the selected artifact exception, and/or the like.

In some embodiments, the artifact information section may display the attributes and properties of a target artifact exception via one or more (e.g., interactable, selectable, and/or editable) user interface elements that are configured to display a current value of a respective attribute and receive input for updating/modifying the current value of respective attribute or property of the target artifact exception to a new value. Example editable user interface elements displayed in the artifact information section may include, but should be limited to, text input fields, dropdown menus, checkboxes, radio buttons, sliders, date pickers, and/or other interactive editable user interface elements. For instance, in a non-limiting example, a text input field implemented by S220 may be configured to receive user input for updating the artifact amount of the target artifact exception. A dropdown menu implemented by S220 may be configured to receive user input for updating the artifact type of the target artifact exception. A checkbox implemented by S220 may be configured to receive user input for updating a binary attribute of the target artifact exception, such as whether the artifact exception is associated with an insurance policy.

Radio buttons implemented by S220 may be configured to receive user input for updating an attribute of the target artifact exception that has multiple, mutually exclusive options. A slider implemented by S220 may be configured to receive user input for updating a numerical attribute of the target artifact exception that falls within a specific range. A date picker implemented by S220 may be configured to receive user input for updating a date-related attribute of the target artifact exception, such as the artifact date. It shall be noted that the above example is not intended to be limiting and that if S210 detected additional input(s) selecting a different artifact exception (or validated artifact), the aforementioned editable user interface elements may, in turn, be updated for modifying the different artifact exception (or validated artifact).

Additionally, as also illustrated in FIG. 5, the artifact information section of the integrated artifact management user interface may include a save button. The save button may be configured to receive user input for saving the user updates made to the attributes or properties of the target artifact exception. In some embodiments, S220 may detect a selection of the save button once the user has inputted the desired attribute updates using the various user interface elements in the artifact information section. In turn, based on detecting the selection, S220 may update the attributes or properties of the target artifact exception in the database in accordance with the user input(s).

Updating a Validated Artifact

Additionally, or alternatively, in some embodiments, modifying at least one artifact may include modifying one or more validated artifacts displayed in the integrated artifact management user interface. Similar to the process of modifying an artifact exception, modifying a validated artifact may include receiving a user input selecting the validated artifact in the first dynamic artifact user interface component (e.g., via the transition control toggle button described herein) and/or may include receiving one or more user inputs for modifying attributes or properties of the currently selected validated artifact. In turn, based on receiving the user input(s), S220 may function to update the attributes or properties of the selected validated artifact in accordance with the user input(s) and save the modified validated artifact to a database storing a plurality of validated artifacts. It shall be noted that the saving of the modified validated artifact may be commenced upon S220 receiving a user input for saving the modified validated artifact (e.g., selecting the "Save" button illustrated in FIG. 6).

It shall also be noted in embodiments where the validated artifacts (e.g., validated artifacts) are selectable for modification (e.g., they are being displayed in the first dynamic artifact user interface component), this may be referred to as displaying the validated artifacts in an editable state. Conversely, if the artifact exceptions are not selectable for modification (e.g., they are being displayed in the second dynamic artifact user interface component), this may be referred to as displaying the validated artifact in an un-editable state.

In some embodiments, upon selecting a validated artifact, S220 may update the integrated artifact management user interface to display details (e.g., attributes or properties) of the selected validated artifact in a similar or analogous way as described above with respect to modifying an artifact exception. That is, in some embodiments, a validated artifact and an artifact exception may have one or more common attributes or properties (e.g., both are associated with a charge amount attribute, an artifact source attribute, an artifact type attribute, an insurance policy attribute, and/or the like).

Furthermore, in a similar manner described with respect to artifact exceptions, S220 may receive one or more user inputs for updating one or more attributes of the validated artifact. The one or more user inputs may be directed to various editable user interface elements of the artifact information section that are specifically configured to receive input for updating a distinct attribute or property of the validated artifact. For instance, in a non-limiting example, S220 may receive user input directed to a text field, a dropdown menu, and/or the like that enables a user to update an artifact amount attribute, an artifact type attribute, and/or the like of the validated artifact. Following the one or more inputs, and also in an analogous manner with respect to saving artifact exceptions, S220 may detect a user input selecting the "save button" to save these updates to a validated artifacts computer database.

Furthermore, in some embodiments, if a value of a respective attribute relates in either the exception artifact or validated artifact relates to an exception, the corresponding editable user interface element may be visually emphasized (e.g., highlighted in red) to indicate such exception to a user.

2.30 Re-Validating Modified Artifacts

S230, which includes re-validating modified artifacts, may function to assess whether modifications made to the artifacts in S220 adhere to a predefined set of artifact validation rules. As will be described in more detail herein, if the re-validation process of S230 determines that a modified artifact (e.g., an artifact exception or a previously validated artifact) does not include any anomalies or errors, the modified artifact may be transitioned to or remain in a "Validated" state. Alternatively, if S230 determines that a modified artifact (e.g., artifact exception or a previously validated artifact) does include at least anomaly or error, the modified artifact may be transitioned to or remain in an "Exception Detected" state.

In some embodiments, the re-validation of a modified artifact may be automatically initiated when method 200 detects a request to save the modified artifact. Upon S230 initiating a re-validation process for a modified artifact, S230 may function to perform a systematic verification of the modified artifact against a predefined set of validation rules. The systematic verification may include comparing the attributes or properties of the modified artifact against the predefined set of validation rules. For example, when S230 detects that a user has saved modifications to a subject artifact, the method 200 may automatically initiate a re-validation process of the subject artifact that includes comparing the attributes of the modified artifact, such as the payer's information and artifact amount, against predefined validation rules. If any discrepancies are detected, the modified artifact may be flagged as an exception. Otherwise, S230 may confirm the modified artifact as a validated artifact.

In some embodiments, the predefined set of artifact validation rules may comprise a variety of rules that are indicative of a successful (valid) artifact. For example, the variety of rules implemented by S230 may include, but should not be limited to, one or more rules for verifying the correctness of a payer's information, one or more rules verifying a validity of an artifact settlement method, one or more rules for verifying an accuracy of an artifact amount, and/or the like. These rules, among others, collectively form the basis of the system re-verification process carried out by S230 and may operate by comparing the attributes or properties of each modified artifact against these rules.

Real-Time Updates to the Integrated Artifact Management User Interface

In some embodiments, when a modified artifact is updated to a new state (e.g., "Exception Detected," "Validated," or the like), S230 may simultaneously update the integrated artifact management user interface to reflect the new state of the artifact. For instance, if a artifact is converted from an "Exception Detected" state to a "Validated" state, S230 may remove (e.g., cease display of) such artifact from the artifact exceptions grid and add it to the validated artifacts grid. Conversely, if an artifact is converted from a "Validated" state to an "Exception Detected" state, S230 may remove (e.g., cease display of) such artifact from the validated artifacts grid and add it to the artifact exception grid. It shall be noted that, in some embodiments, converting an artifact from an "Exception Detected" state to a "Validated" state may be referred to as converting the exception artifact to a validated artifact (or vice versa).

Additionally, or alternatively, in some embodiments, if a state of a artifact remains unchanged after validation, S230 may continue to display the artifact in the grid where it is currently being displayed. For example, an artifact that remains in the "Validated" state after requalification may continue to be displayed in the validated artifacts grid. Similarly, an artifact that remains in the "Exception Detected" state after failing requalification may continue to be displayed in the artifact exceptions grid.

It shall be noted that this real-time update of the integrated artifact and exception management user interface may enable many technical advantages including, but not limited to, providing users with an accurate and up-to-date view of the artifact processing status, thus enhancing the efficiency and accuracy of the artifact processing.

2.40 Posting Validated Artifacts

S240, which includes posting validated artifacts, may function to post (e.g., publish) one or more of the validated artifacts to corresponding patient accounts. Upon posting a validated artifact to a patient account (e.g., user account), S240 may update a status of the validated artifact to reflect that such artifact has been successfully posted. For example, S240 may change the status of the artifact from 'validated' to 'posted,' indicating a completion of the artifact processing workflow.

Figure 6:
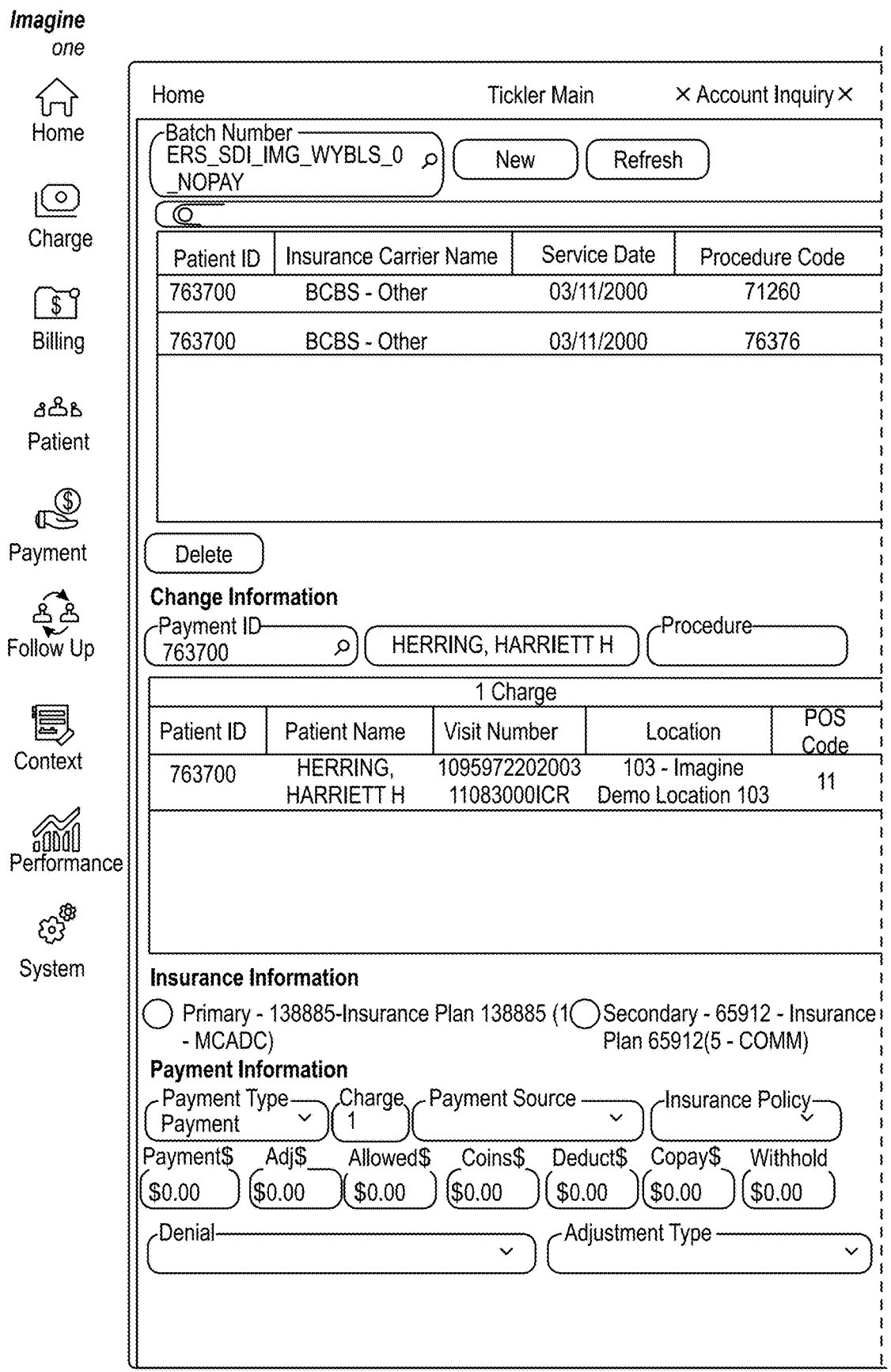

In some embodiments, a validated artifact may be posted upon (e.g., in response to) receiving a user input. For instance, as illustrated in FIG. 6, S240 may function to post the validated artifact selected in FIG. 6 upon receiving a user input selecting the 'Post' button. In turn, based on detecting the user input selecting the 'Post' button, S240 may additionally function to transition the validated artifact to the "posted" stage. It shall be noted that while FIG. 6 describes posting a validated artifact via a selectable button, other methods of initiating the posting process may additionally or alternatively be implemented without departing from the scope of the disclosure.

Furthermore, in some embodiments, once a validated artifact has been successfully posted, S240 may also update the integrated artifact management user interface to reflect the new status of the posted artifact(s). For instance, the posted artifacts may be removed from the validated artifacts grid. It shall be noted that this real-time update of the user interface may result in many technical advantages including providing users with an accurate and up-to-date view of the artifact processing status, thereby enhancing the efficiency and accuracy of the artifact processing workflow.

Dynamic Grid Layout Controls

In some instances, the integrated artifact management user interface may include a toggle button, sometimes referred to as a transition control toggle button, that allows users to swap positions of the validated artifacts grid and the artifacts exceptions grid in the integrated artifact management user interface. For instance, as illustrated in FIG. 5, the artifact exceptions grid may initially be displayed at a top portion of the integrated artifact management user interface, and the validated artifacts grid may initially be displayed at a bottom portion of the integrated artifact management user interface. In such an example, upon or in response to detecting a selection of the toggle button, S240 may swap the positions of the validated artifacts grid and the artifact exceptions grid, as generally illustrated in FIG. 6. Specifically, the artifacts grid may move to the top portion of the integrated artifact management user interface, and the artifact exceptions grid may move to the bottom portion of the integrated artifact management user interface.

Conversely, in a second example, the validated artifacts grid may initially be displayed at the bottom portion of the integrated artifact management user interface, and the artifact exceptions grid may initially be displayed at the top portion of the integrated artifact management user interface. In such an example, upon or in response to detecting a selection of the toggle button, S240 may swap the positions of the validated artifacts grid and the artifact exceptions grid. Specifically, the artifacts exceptions grid may move to the bottom portion of the integrated artifact management user interface, and the validated artifacts grid may move to the top portion of the integrated artifact management user interface. It shall be noted that providing such a toggle button in the integrated artifact management user interface may result in many technical advantages including enhanced control over the organization and management of artifact processing tasks, thereby facilitating a more efficient and accurate workflow by allowing users to customize the layout of the validated artifacts grid and artifact exceptions grid.

Stated another way, the toggle button may be associated with a plurality of toggle states. Each toggle state may correspond to and be displayed during a specific period. For instance, during a first period, the toggle button may be in a "Edit Exceptions" state. In this first period (e.g., the "Edit Exceptions" state), the first dynamic artifact user interface component (e.g., the table displayed at the top of the user interface of in FIG. 5), may display a corpus of exception artifacts. Additionally, in this first period, the second dynamic user interface component (e.g., the table displayed in the lower right portion of the user interface in FIG. 5), may display a corpus of validated artifacts. It shall be noted that, for the reasons described previously, the corpus of exception artifacts and the corpus of validated artifacts may be in an "editable state" and "un-editable state," respectively.

In some embodiments, selecting the toggle button may cause a state of the toggle button to change. For example, if the state of the toggle button corresponds to the "Edit Exceptions" state, a selection of the toggle button may cause the state of the toggle button to change from the "Edit Exceptions" state to a "Edit Validated Artifacts" state. Conversely, in some embodiments, if the state of the toggle button corresponds to the "Edit Validated Artifacts" state, a selection of the toggle button may cause the state of the toggle button to change from the "Edit Validated Artifacts" state to a "Edit Exceptions" state.

In some embodiments, the state of the toggle button may correspond to the "Edit Exceptions" state during a first period and a "Edit Validated Artifacts" state during a second period. In this second period (e.g., the "Edit Validated Artifacts" state), method 200 may transition the first dynamic artifact user interface component (e.g., the table displayed at the top of the user interface of in FIG. 5) from displaying a corpus of exception artifacts during the first period to displaying a corpus of validated artifacts during the second period as illustrated in FIGS. 5 and 6, respectively. Additionally, in this second period (e.g., the "Edit Validated Artifacts" state), method 200 may transition the second dynamic user interface component (e.g., the table displayed in the lower right portion of the user interface in FIG. 5) from displaying a corpus of validated artifacts to displaying a corpus of exception artifacts as illustrated in FIGS. 5 and 6, respectively.

It shall be noted that when the corpus of exception artifacts are displayed in the first dynamic artifact user interface component in FIG. 5, the corpus of exception artifacts may be described as being in an editable state, and when the corpus of exception artifacts are displayed in the second dynamic artifact user interface component in FIG. 6, the corpus of exception artifacts may be described as being in an un-editable state until promoted to the first dynamic artifact user interface component.

Analogously, it shall be noted that when the corpus of validated artifacts are displayed in the second dynamic artifact user interface component in FIG. 5, the corpus of validated artifacts may be described as being in an un-editable state, and when the corpus of validated artifacts are displayed in the first dynamic artifact user interface component in FIG. 6, the corpus of validated artifacts may be described as being in an editable state.

In some embodiments, the dynamic artifact user interface components may include additional details in the table headers and layout. For example, during the first period, the first dynamic artifact user interface component may include a table header that indicates the total number of exception artifacts, the total value associated with the corpus of exception artifacts, and the total adjustment value associated with these exception artifacts. During the second period, the same table header may transition to display the total number of validated artifacts within the corpus of validated artifacts. Likewise, the second dynamic artifact user interface component may adapt to these periods. In the first period, the second dynamic artifact user interface component may display a table header with the total number of validated artifacts, while in the second period, it may shift (e.g., transition) to display the total number of exception artifacts, their total value, and total adjustment value.

The arrangement of artifact data within the interface may evolve in parallel with these transitions. During the first period, the first dynamic artifact user interface component may present a set of attribute exception columns and corresponding rows for exception artifacts. However, in the second period, this component may adjust to display validated attribute columns for the validated artifacts. Similarly, the second dynamic artifact user interface component may display a subset of validated attribute columns and corresponding rows during the first period, then transition to show a subset of the exception attribute columns during the second period, as will be described below.

In terms of layout, the multi-artifact handling user interface may be divided into distinct sections. In some embodiments, the upper section may contain the first dynamic artifact user interface component, spanning substantially the full width of this section, while the lower section may include a set of editable user interface elements and the second dynamic artifact user interface component, with the layout spanning the width from the start to the middle and from the middle to the end, respectively. Alternatively, the interface may include an upper, middle, and lower section, where each component—first dynamic, second dynamic, and editable elements—spans substantially the full width of their respective sections.

The method 200, in some embodiments, may further include functionality for displaying specific columns within these dynamic artifact components. For instance, during the first period, the first dynamic artifact user interface component may display the corpus of exception artifacts associated with a full set of attribute exception columns. During the second period, when the second dynamic artifact user interface component displays the exception artifacts, it may do so using a subset of these columns to offer a more focused view. This set of attribute exception columns may include key fields such as an entity identifier, exception message, reason code, entity name, and coverage provider, while other fields, such as service date, service code, service value, allocation value, record identifier, and modification value, may be excluded from the subset displayed.

Additionally, in some embodiments, the dynamic artifact user interface components may further include functionality for transitioning between different sets of validated attribute columns across the first and second periods. For example, during the first period, the second dynamic artifact user interface component may display the corpus of validated artifacts in association with a set of validated attribute columns. These columns may include an entity identifier column, a coverage provider column, a service date column, a service code column, an allocation value column, and a modification value column. However, when the transition control toggle button is selected, and the first dynamic artifact user interface component begins displaying the corpus of validated artifacts during the second period, the interface may expand to display a superset of validated attribute columns. This superset may include the set of validated attribute columns from the first period and additional columns for a more comprehensive view.

The additional columns displayed during the second period, as part of the superset, may include fields such as a modification type column, a permitted value column, a shared responsibility value column, an initial requirement value column, and a fixed contribution amount column. This expanded set of columns may provide users with a broader and more detailed understanding of the validated artifacts during the second period, allowing for more granular insight.

3. Computer-Implemented Method and Computer Program Product

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

The system and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processors and/or the controllers. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that similar to a method with contingent steps, a system or computer readable storage medium can repeat the steps of a method as many times as are needed to ensure that all of the contingent steps have been performed.

Although omitted for conciseness, the preferred embodiments include every combination and permutation of the implementations of the systems and methods described herein.

As a person skilled in the art will recognize from the previous detailed description and from the figures and claims, modifications and changes can be made to the preferred embodiments of the invention without departing from the scope of this invention defined in the following claims.

I claim:

1. A method for concurrently handling multiple artifact types in a unified graphical user interface, the method comprising:
displaying a multi-artifact handling user interface for concurrently handling a corpus of exception artifacts and a corpus of validated artifacts, wherein the multi-artifact handling user interface includes:
a first dynamic artifact user interface component that displays the corpus of exception artifacts in an editable state during a first period,
a second dynamic artifact user interface component that displays the corpus of validated artifacts in an un-editable state during the first period,
a transition control toggle button that is selectable to transition:
the first dynamic artifact user interface component from displaying the corpus of exception artifacts to displaying the corpus of validated artifacts during a second period, and
the second dynamic artifact user interface component from displaying the corpus of validated artifacts to displaying the corpus of exception artifacts during the second period, and
a plurality of editable user interface elements for modifying a plurality of attributes of an exception artifact selected in the first dynamic artifact user interface component during the first period;
detecting an input selecting the transition control toggle button; and
based on detecting the input selecting the transition control toggle button:
updating the first dynamic artifact user interface component to display the corpus of validated artifacts in the editable state during the second period,
updating the second dynamic artifact user interface component to display the corpus of exception artifacts in the un-editable state during the second period, and
updating the plurality of editable user interface elements to modify a plurality of attributes of a validated artifact selected in the first dynamic artifact user interface component during the second period.

2. The method according to claim 1, wherein:
a respective editable user interface element of the plurality of editable user interface elements:
corresponds to a respective attribute of the plurality of attributes of the exception artifact,
includes a value of the respective attribute in the exception artifact, and
is visually emphasized to indicate that the value of the respective attribute relates to an exception.

3. The method according to claim 2, further comprising:
during the first period:
receiving, via the respective editable user interface element, a first input for changing the value of the respective attribute that relates to the exception to a new value that resolves the exception;
receiving, via the multi-artifact handling user interface, a second input for modifying, in a computer database, the exception artifact to include the new value of the respective attribute; and
based on receiving the first input and the second input:
modifying, in the computer database, a record corresponding to the exception artifact to include the new value of the respective attribute that resolves the exception;

ceasing display of the exception artifact in the first dynamic artifact user interface element based on the new value of the respective attribute resolving the exception for the exception artifact;
converting, in the computer database, the exception artifact to a new validated artifact; and
adding the new validated artifact to the second dynamic artifact user interface component.

4. The method according to claim 1, wherein:
during the first period, the first dynamic artifact user interface component includes a table header that indicates:
a total number of exception artifacts included in the corpus of exception artifacts,
a total value associated with the corpus of exception artifacts, and
a total adjustment value associated with the corpus of exception artifacts, and
during the second period, the table header of the first dynamic artifact user interface component includes:
a total number of validated artifacts included in the corpus of validated artifacts.

5. The method according to claim 4, wherein:
during the first period, the second dynamic artifact user interface includes a table header that includes:
the total number of validated artifacts included in the corpus of validated artifacts, and
during the second period, the table header of the second dynamic artifact user interface includes:
the total number of exception artifacts included in the corpus of exception artifacts,
the total value associated with the corpus of exception artifacts, and
the total adjustment value associated with the corpus of exception artifacts.

6. The method according to claim 1, wherein:
during the first period, the first dynamic artifact user interface component includes a set of attribute exception columns and a plurality of rows corresponding to the corpus of exception artifacts, and
during the second period, the first dynamic artifact user interface component includes a set of validated attribute columns and a plurality of rows corresponding to the corpus of validated artifacts.

7. The method according to claim 6, wherein:
during the first period, the second dynamic artifact user interface component includes a subset of the set of validated attribute columns and the plurality of rows corresponding to the corpus of validated artifacts, and
during the second period, the second dynamic artifact user interface component includes a subset of the set of attribute exception columns and the plurality of rows corresponding to the corpus of exception artifacts.

8. The method according to claim 1, wherein:
the multi-artifact handling user interface includes an upper section and a lower section,
the upper section of the multi-artifact handling user interface includes the first dynamic artifact user interface component with a width that spans substantially a full width of the upper section, and
the lower section includes:
the plurality of editable user interface elements with a width that substantially spans from a start of the lower section to a middle of the lower section, and
the second dynamic artifact user interface component with a width that substantially spans from the middle of the lower section to an end of the lower section.

9. The method according to claim 1, wherein:
the multi-artifact handling user interface includes an upper section, middle section, and a lower section,
the upper section of the multi-artifact handling user interface includes the first dynamic artifact user interface component with a width that spans substantially a full width of the upper section,
the middle section of the multi-artifact handling user interface includes the second dynamic artifact user interface component with a width that spans substantially a full width of the middle section, and
the lower section includes the plurality of editable user interface elements with a width that substantially spans with a width that spans substantially a full width of the lower section.

10. The method according to claim 1, wherein:
displaying the corpus of exception artifacts in the first dynamic artifact user interface component during the first period includes:
displaying the corpus of exception artifacts in association with a set of attribute exception columns, and
transitioning, via the transition control toggle button, the second dynamic artifact to displaying the corpus of exception artifacts during the second period includes:
displaying the corpus of exception artifacts in association with a subset of the set of attribute exception columns, wherein the subset of the set of attribute exception columns is less than a full size of the set of attribute exception columns.

11. The method according to claim 10, wherein the set of attribute exception columns and the subset of the set of attribute exception columns at least includes:
an entity identifier column,
an exception message column,
a reason code column,
an entity name column, and
a coverage provider column.

12. The method according to claim 11, wherein one or more attribute exception columns included in the set of attribute exception columns that are not included in the subset of the set of attribute exception columns at least comprises:
a service date column,
a service code column,
a service value column,
an allocation value column,
a record identifier column, and
a modification value column.

13. The method according to claim 1, wherein:
the multi-artifact handling user interface further includes an artifact batch selection dialog user interface element comprising a plurality of selection entries corresponding to a plurality artifact validation-exception batches, and
the method further comprises:
receiving, via the artifact batch selection dialog user interface element, an input selecting a target selection entry of the plurality of selection entries; and
based on receiving the input selecting the target selection entry:
identifying a respective validation-exception batch of the plurality of artifact validation-exception batches that corresponds to the target selection entry;
obtaining, from a computer database, the corpus of exception artifacts associated with the respective validation-exception batch; and obtaining, from the computer database, the corpus of validated artifacts associated with the respective validation-exception batch.

14. The method according to claim 1, wherein:
the exception artifact selected in the first dynamic artifact user interface component during the first period corresponds to a first exception artifact in the corpus of exception artifacts, and
the method further comprises:
during the first period:
receiving, via the first dynamic artifact user interface component, an input for changing the exception artifact selected in the first dynamic artifact user interface component from the first exception artifact to a second exception artifact in the corpus of exception artifacts; and
in response to receiving the input for changing the exception artifact selected in the first dynamic artifact user interface component from the first exception artifact to the second exception artifact, updating the plurality of editable user interface elements from modifying the plurality of attributes of the first exception artifact to modifying the plurality of attributes associated with the second exception artifact.

15. The method according to claim 1, wherein:
the validated artifact selected in the first dynamic artifact user interface component during the second period corresponds to a first validated artifact in the corpus of validated artifacts, and
the method further comprises:
during the second period:
receiving, via the first dynamic artifact user interface component, an input for changing the validated artifact selected in the first dynamic artifact user interface component from the first validated artifact to a second validated artifact in the corpus of validated artifacts; and
in response to receiving the input for changing the validated artifact selected in the first dynamic artifact user interface component from the first validated artifact to the second validated artifact, updating the plurality of editable user interface elements from modifying the plurality of attributes of the first validated artifact to modifying the plurality of attributes associated with the second validated artifact.

16. The method according to claim 1, wherein:
displaying the corpus of validated artifacts in the second dynamic artifact user interface component during the first period includes:
displaying the corpus of validated artifacts in association with a set of validated attribute columns, and
transitioning, via the transition control toggle button, the first dynamic artifact to displaying the corpus of validated artifacts during the second period includes:
displaying the corpus of validated artifacts in association with a superset of validated attribute columns, wherein the superset of validated attribute columns includes the set of validated attribute columns.

17. The method according to claim 16, wherein the set and superset of validated attribute columns at least includes:
an entity identifier column,
a coverage provider column,
a service date column,
a service code column,
an allocation value column, and
a modification value column.

18. The method according to claim 17, wherein one or more validated attribute columns included in the superset of validated attribute columns that are not included in the set of validated attribute columns at least comprises:
a modification type column,
a permitted value column,
a shared responsibility value column,
an initial requirement value column, and
a fixed contribution amount column.

19. A computer-program product comprising a non-transitory machine-readable storage medium storing computer instructions that, when executed by one or more processors, perform operations comprising:
displaying a multi-artifact handling user interface for concurrently handling a corpus of exception artifacts and a corpus of validated artifacts, wherein the multi-artifact handling user interface includes:
a first dynamic artifact user interface component that displays the corpus of exception artifacts in an editable state during a first period,
a second dynamic artifact user interface component that displays the corpus of validated artifacts in an un-editable state during the first period,
a transition control toggle button that is selectable to transition:
the first dynamic artifact user interface component from displaying the corpus of exception artifacts to displaying the corpus of validated artifacts during a second period, and
the second dynamic artifact user interface component from displaying the corpus of validated artifacts to displaying the corpus of exception artifacts during the second period, and
a plurality of editable user interface elements for modifying a plurality of attributes of an exception artifact selected in the first dynamic artifact user interface component during the first period;
detecting an input selecting the transition control toggle button; and
based on detecting the input selecting the transition control toggle button:
updating the first dynamic artifact user interface component to display the corpus of validated artifacts in the editable state during the second period,
updating the second dynamic artifact user interface component to display the corpus of exception artifacts in the un-editable state during the second period, and
updating the plurality of editable user interface elements to modify a plurality of attributes of a validated artifact selected in the first dynamic artifact user interface component during the second period.

20. A computer-implemented system comprising:
one or more processors;
a memory; and
a computer-readable medium operably coupled to the one or more processors, the computer-readable medium having computer-readable instructions stored thereon that, when executed by the one or more processors, cause a computing device to perform operations comprising:
displaying a multi-artifact handling user interface for concurrently handling a corpus of exception artifacts and a corpus of validated artifacts, wherein the multi-artifact handling user interface includes:

a first dynamic artifact user interface component that displays the corpus of exception artifacts in an editable state during a first period, a second dynamic artifact user interface component that displays the corpus of validated artifacts in an un-editable state during the first period, a transition control toggle button that is selectable to transition:
  the first dynamic artifact user interface component from displaying the corpus of exception artifacts to displaying the corpus of validated artifacts during a second period, and
  the second dynamic artifact user interface component from displaying the corpus of validated artifacts to displaying the corpus of exception artifacts during the second period, and a plurality of editable user interface elements for modifying a plurality of attributes of an exception artifact selected in the first dynamic artifact user interface component during the first period;

detecting an input selecting the transition control toggle button; and based on detecting the input selecting the transition control toggle button:
  updating the first dynamic artifact user interface component to display the corpus of validated artifacts in the editable state during the second period,
  updating the second dynamic artifact user interface component to display the corpus of exception artifacts in the un-editable state during the second period, and
  updating the plurality of editable user interface elements to modify a plurality of attributes of a validated artifact selected in the first dynamic artifact user interface component during the second period.

\* \* \* \* \*